United States Patent [19]

Kato et al.

[11] Patent Number: 4,639,838

[45] Date of Patent: Jan. 27, 1987

[54] SHADOWLESS LIGHTING EQUIPMENT FOR MEDICAL USE

[75] Inventors: Yasuhiro Kato; Mitsuhiro Koyama, both of Tokyo, Japan

[73] Assignee: Yamada Iryo Shomei Kabushiki Kaisha, Tokyo, Japan

[21] Appl. No.: 793,979

[22] Filed: Nov. 1, 1985

[30] Foreign Application Priority Data

Mar. 30, 1985 [JP] Japan .................................. 60-65058

[51] Int. Cl.[4] .......................... F21M 1/00; A61B 6/08

[52] U.S. Cl. ...................................... 362/33; 362/804; 362/287; 378/206

[58] Field of Search ................. 362/33, 802, 804, 285, 362/286, 287; 250/203 R; 378/165, 166, 205, 206; 358/111, 113

[56] References Cited

U.S. PATENT DOCUMENTS

| | | | |
|---|---|---|---|
| 3,861,807 | 1/1975 | Lescrenier | 378/206 |
| 3,967,107 | 6/1976 | Junginger et al. | 362/33 |
| 4,578,575 | 3/1986 | Roos | 362/804 |
| 4,589,126 | 5/1986 | Augustsson | 378/205 |

*Primary Examiner*—William A. Cuchlinski, Jr.
*Assistant Examiner*—D. M. Cox
*Attorney, Agent, or Firm*—Wenderoth, Lind & Ponack

[57] ABSTRACT

A shadowless lighting equipment for medical use includes an illuminating device for emitting a wave beam such as an infrared ray beam subjected to frequency modulation on a patient on an operating table so as to form an irradiation area thereon, an image forming device which forms an image of the irradiation area in accordance with a wave beam reflected from the irradiated portion of the patient, and a sensor for comparing information regarding an image forming position by the image forming device with information regarding a light concentration position of a lighting device. In this comparison, when the image forming position is spaced apart from the light concentration position, an output containing information regarding the positional difference between the positions is provided, and, in response to such an output, the lighting device is driven in the X axis, Y axis, and perpendicular directions of a coordinate surface so that the light concentration position becomes the same as the image forming position.

10 Claims, 11 Drawing Figures

SHADOWLESS LIGHTING EQUIPMENT FOR MEDICAL USE

BACKGROUND OF THE INVENTION

This invention relates to shadowless lighting equipment for medical use particularly capable of automatically focusing or concentrating the light on a desired portion of a patient on an operating table.

Generally, it is required that lighting equipment for medical use irradiate a person on an operating table or bed during the operation with a light without projecting shadows thereon and to easily adjust the lighting or irradiating conditions. Particularly, it has been desired to provide lighting equipment which can freely adjust the light concentration position in accordance with the intentions of a person who carries out an operation, called an operator hereinafter, during the operation.

One example of the lighting equipment of the type described above is disclosed in Japanese Patent Publication No. 25,681/1970, and this prior art of lighting equipment will be explained hereunder with reference to FIG. 1. Referring to FIG. 1, a lighting device 1' including a plurality of lamps is located on the upper portion so as to irradiate a person 2 to be operated on, called a patient hereinafter, with a light from the upper portion, and an illuminating device 3' is located between the lighting device 1' and the patient 2 to adjust the focusing or concentration position of the lighting device 1'. In an actual operation, the operator moves the illuminating device 3' to a desired portion to project frequency-modulated waves towards the lighting device 1' as shown by dot and dashed lines in FIG. 1. The light waves emitted from the illuminating device 3' are received by a light receiving unit 4' contained in the lighting device 1' so as to thereby be controlled so that an irradiation light, shown by a solid line, from the lighting device 1' can be concentrated on the predetermined position of the illuminating device 3'.

According to the manner described above, the operator can obtain a desired irradiation light only by designating the light concentration position through the illuminating device 3'.

However, in an actual operation using the lighting equipment of the prior type described above, it is difficult to accurately concentrate the light on a desired position of the patient on the operating table, this being a severe problem in the medical field.

It is also necessary to maintain an antiseptic condition in an operating room during the operation to prevent a secondary infection of a pathogenic bacteria in the patient and it is particularly necessary to maintain cleanliness of the portion of the patient to be operated on. The direct contact of foreign matter to the portion to be operated on should also be absolutely avoided. The concentration of the light from the lighting equipment on the portion to be operated on is of course required in almost all cases during the operation, and for example, in a case where it is necessary to designate the portion 5 of the patient 2 to be operated on, hatched in FIG. 1, as the light concentrating position, it is necessary to directly contact the illuminating device 3' to the portion 5 to be operated on when using the prior type lighting equipment, this being not desired from the point of view of causing a secondary infection through the illuminating device 3'.

Accordingly, in the actual operation of the prior art type of equipment, it is very difficult to concentrate the light accurately on the desired portion of the patient 2 on the operating table without causing the problems described above.

SUMMARY OF THE INVENTION

An object of this invention is to eliminate problems and disadvantages of the prior art equipment and provide an improved shadowless lighting equipment for medical use capable of accurately and automatically concentrating a light on a required portion of a patient to be operated on.

According to this invention, in order to achieve this and other objects, a shadowless lighting equipment for medical use is provided comprising a lighting device for lighting a person on an operating table who is to be operated on, an illuminating device for emitting a wave beam, such as infrared ray beam, on a predetermined portion of the person on the operating table to form an irradiation area thereon, an image forming means which forms an image of the irradiation area in accordance with a wave beam reflected from the predetermined portion of the person on the operating table, a sensor for comparing data regarding an image forming position by the image forming means which data regarding a light concentration position of the lighting device and for generating an output containing data regarding a directional difference between the image forming position and the light concentration position when the former position is shifted from the latter position, and a mechanism for driving the lighting device in response to the output from the sensor so that the light concentration position corresponds with the image forming position.

The nature, utility, and further features of this invention will be more clearly apparent from the following detailed description with respect to the preferred embodiment of this invention when read in conjunction with the accompanying drawings, briefly described below.

DESCRIPTION OF THE PREFERRED EMBODIMENTS

Figure 1:
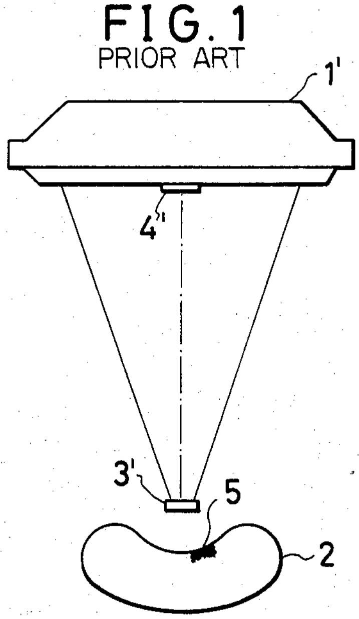
FIG. 1 PRIOR ART
FIG. 1 is a brief illustration of lighting equipment for medical use of a prior art type.
Figure 2A:
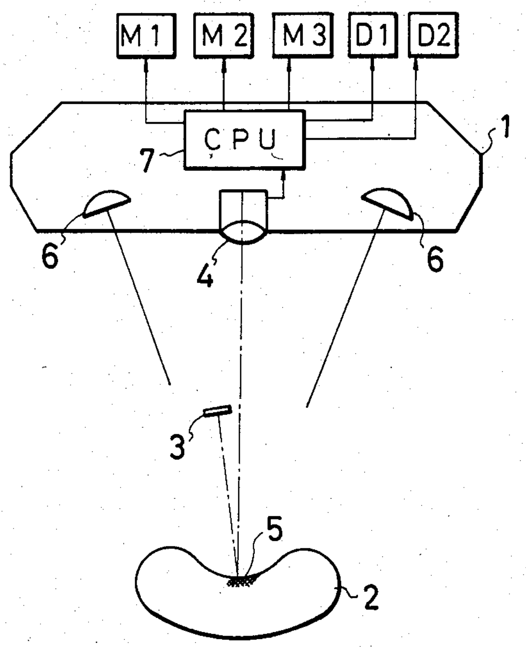
FIG. 2A is also an illustration of a shadowless lighting equipment for medical use according to this invention.

Referring to FIG. 2A which briefly illustrates one preferred embodiment of the lighting equipment according to this invention, in which a lighting device 1 contains a plurality of lighting lamps 6 and a light receiving unit 4 of the type similar to those of the prior art. An illuminating device 3, such as a wave beam generator, located between the lighting device 1 and a patient 2 on an operation table emits an infrared ray beam subjected to a predetermined frequency modulation. Assuming that the portion 5 of the patient 2 to be operated on is designated as the portion on which the light should be concentrated, an irradiation area is formed on the portion 5 of the patient 2 by emitting the infrared ray beam towards the portion 5 from the illuminating device 3 located at any optional position, and in this irradiation operation, there is no fear of causing a secondary infection because the use of infrared rays obviates the need for actual physical contact with the patient 2.

The light receiving unit 4, as described in detail hereinafter, receives the infrared rays reflected from the irradiated area and detects the positional difference between the irradiation area and the light concentrated position. The detected positional difference is fed to a central processing unit (CPU) 7 as a detection signal. The CPU 7 then transmits control signals in response to the detected signal so as to thereby operate electric motors M1, M2, and M3, and clutch means D1 and D2 which move the lighting device 1 until the irradiated area and the light concentration position coincide.

Figure 2B:
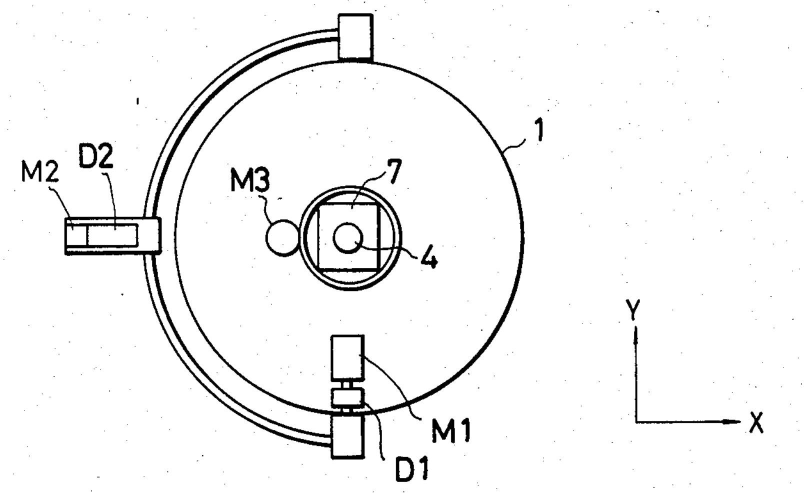
FIG. 2B is a plan view of a lighting device of the lighting equipment shown in FIG. 2A as viewed from the lower side thereof.

FIG. 2B shows a plan view of the lighting device 1 according to this invention as viewed from the lower side thereof in FIG. 2A. Referring to FIG. 2B, the electric motors M1, M2, and M3, which are operatively connected to the CPU 7, respectively drive the lighting device 1 in an X-direction, a Y-direction and a Z-direction (perpendicular direction with respect to the surface of the drawing), and the clutch means D1 and D2 are used for the drive shaft couplings of the motors M1 and M2, respectively. The motor M3 for driving the lighting device 1 in the Z-direction is used for adjusting the focus of the lighting device 1. By this associated operation of these motors and the clutch means, the lighting device 1 is moved in a desired direction so as to thereby concentrate the light on a predetered portion, and the light receiving unit 4 is also operated or moved together with the lighting device 1.

The infrared ray beam emitted from the illuminating device 3 advances along the path shown by dot and dashed lines in FIG. 2A because the infrared rays are subjected to frequency modulation so as to thereby provide positional information to the CPU 7, as well as information regarding the focus, the illumination intensity, the operation mode, and the like.

Although in the preferred embodiment described herein, an infrared ray beam is utilized, it will easily be understood that a light wave with a different frequency, an electromagnet wave, an acoustic wave, or other wave beams which do not adversely affect the patient, may be utilized for the purpose of performing the operation according to this invention.

The light receiving device 4 generally comprises an image forming means 4a and a light receiving sensor 4b, and a lens system is preferably used in the subject embodiment, but any other means such as pin hole means which forms an image on the light receiving sensor 4b may also be used. When the acoustic wave is utilized as a wave beam, the use of an image forming means suitable for the acoustic wave and an acoustic wave sensor will be naturally understood. A wave beam projected so as to be parallel to the optical axis of the image forming means 4a is formed as an image on the central point 0 of the light receiving sensor 4b.

Figure 3A:
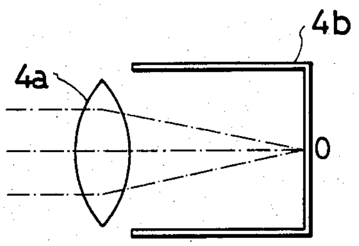
FIGS. 3A and 3B are simplified partial longitudinal sectional views of a light receiving sensor to be used for the lighting equipment shown in FIG. 2A.
Figure 3B:
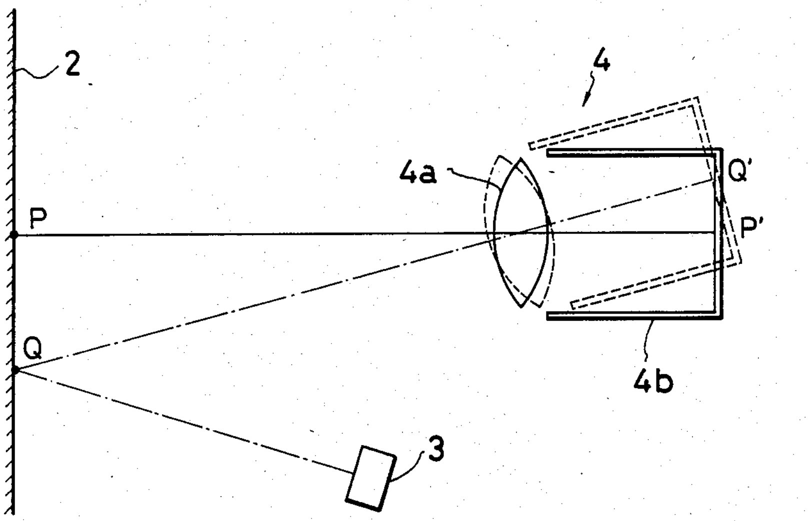

The principle of the light concentration position change operation of the lighting equipment according to this invention will be described hereunder with reference to FIGS. 3A and 3B in which a light concentrating position of the lighting device 1 on the patient 2 is not illustrated as a point P and the light receiving unit 4 consists of the lens system 4a and the light receiving sensor 4b. In a case where the light concentrating position of the lighting device 1 is now the point P, the image of the point P is formed through the lens system 4a on a point P', i.e. the central point 0 of the light receiving sensor 4b.

The operator changes the light concentrating position P to a position Q on the patient 2 by the irradiation of the infrared ray on the point Q with the illuminating device 3. The light image on the point Q is formed on a point Q' of the light receiving sensor 4b is offset from the central point 0, as represented by the lines in FIG. 3B representing the path of the infrared ray beam. Then, the point Q is shifted so as to correspond to the central point 0 of the light receiving sensor 4b by moving the lighting device 1 through the driving of the respective motors M1, M2, and M3. During this operation, the light receiving unit 4 moves together with the lighting device 1 and when the point Q' corresponds to the central point 0 of the light receiving sensor 4b, the driving operation of the motors M1 through M3 stops, and thus, the light concentrating position P is automatically moved to the point Q.

Figure 4A:
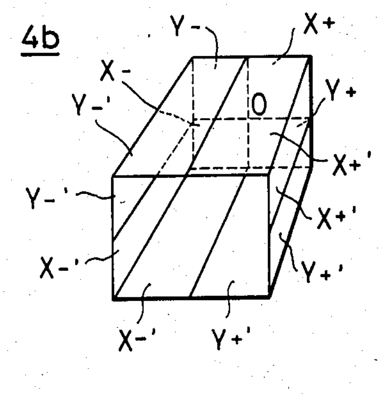
FIG. 4A shows a perspective view of a light receiving sensor of the light receiving device shown in FIGS. 3A and 3B.
Figure 4B:
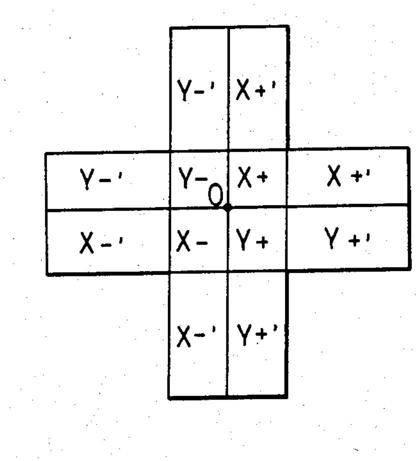
FIG. 4B shows a development of the light receiving sensor shown in FIG. 4A.

FIG. 4A is a perspective view of the light receiving sensor 4b used for the lighting equipment according to this invention and FIG. 4B shows the development of the sensor 4b shown in FIG. 4A. Referring to these figures, around the central point 0 are disposed detecting portions X+ and X− for detecting the shift in the X axis direction and detecting portions Y+ and Y− for detecting the shift in the Y axis direction.

In case the distance between the image formed point and the central point 0 is not very large and is within a predetermined range, the shifting operation can be done by providing only four detecting portions around the point 0 described above, but according to this invention, four further detecting portions X+', X−', Y+', and Y−' are provided as shown in FIG. 4A and by taking into consideration a case where the distance between the image formed point and the central point 0 is relatively large. Accordingly, when the image formed point resides in the detecting portion X+ or X+', the motor M1 is driven so as to thereby move the lighting device in the negative X axis direction, while being driven in the positive X axis direction when the image formed point resides in the X− or X−' portion. The Y axis directional control of the lighting device 1 can be effected in substantially the same manner as described with respect to the X axis directional control. In this manner, the lighting device 1 can be moved in such a direction as that the image formed point will always correspond to the central point 0 of the light receiving sensor 4b.

Figure 5:
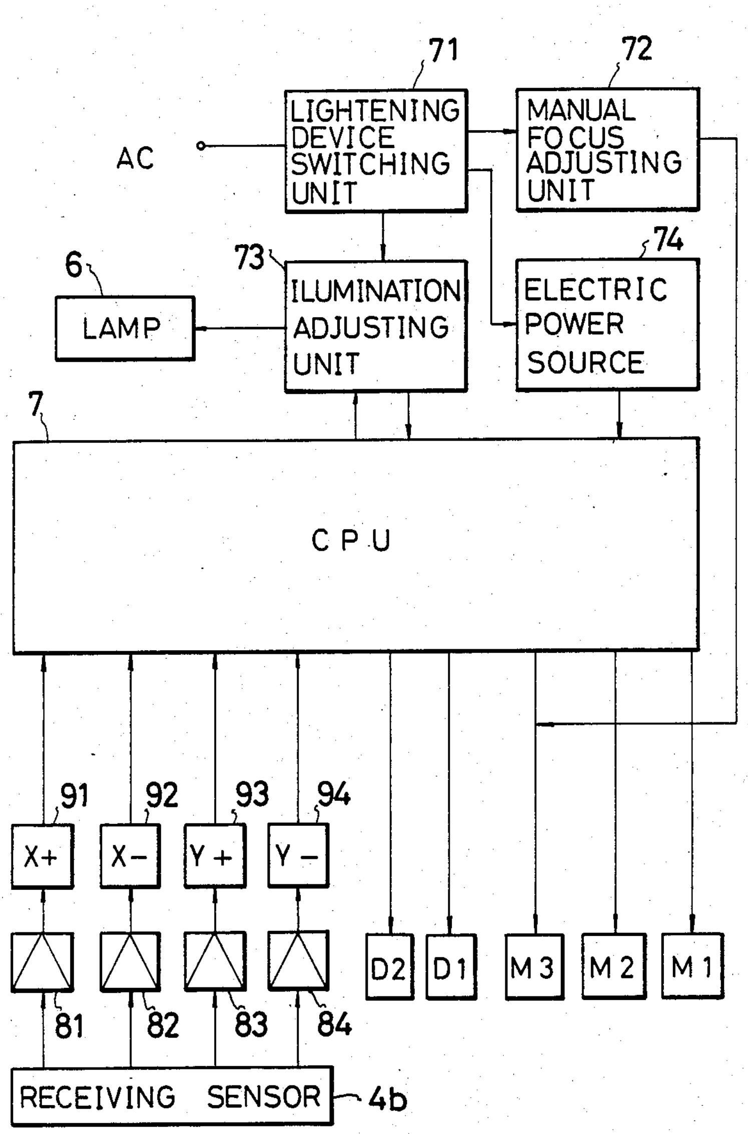
FIG. 5 shows a block diagram of the shadowless type lighting equipment according to this invention.

FIG. 5 shows a block diagram of the lighting equipment according to this invention.

Referring to FIG. 5, a switching unit 71 adapted to manage the various operations of the lighting device 1 is disposed on the side thereof, and an alternating current (a.c.) is supplied to the switching unit 71 from an external a.c. source and then supplied into a power source unit 74 through a power switch. The a.c. supplied to the power source unit 74 is changed into a predetermined form therein (e.g.—regulated low voltage D.C.) and then fed to the CPU 7 as its drive power. When it is necessary to carry out the forcus adjustment of the lighting device, an operation signal is transmitted from switching unit 71 to a manual focus adjusting unit 72, and the focus adjustment is carried out by driving of the motor M3 in response to the operation signal from the switching unit.

Furthermore, when it is necessary to carry out the illumination adjustment, an operation signal is transmitted there the switching unit 71, to an illumination adjusting unit 73, and the illumination adjustment is carried out by adjusting the electric power to be supplied to the lighting lamps 6 in response to the operation from the switching unit 71.

Although in the foregoing description, a manual operation is referred to, automatic adjusting operations effected by the use of the illuminating device 3 as a remote control device are all carried out in accordance with the information detected by the light receiving sensor 4*b*.

Namely, referring to FIG. 5, the information regarding the light concentration position change are fed to detectors 91, 92, 93, and 94 through amplifiers 81, 82, 83, and 84, with respect to respective outputs from the detecting portions X+(or X+'), X−(or X−'), Y+(or Y+'), and Y−(or Y−') of the sensor 4*b*. In accordance with the information detected by the detectors 91 through 94, the CPU 7 operates so as to control the operations of the motors M1, M2, and M3 and the clutch means D1 and D2 so as to thereby change the light concentration position. The information regarding the focus adjustment and the illumination adjustment are transferred to the CPU 7 through the light receiving sensor 4*b* by modulating the infrared ray, and the CPU 7 carries out the focus adjustment by driving the motor M3 and the illumination adjustment in association with the illumination adjusting unit 73.

With the foregoing embodiment, although a case is described in which the light concentration position is controlled by the reflected beam from the desired position of the patient, it will of course be understood that, in a case where there is no problem for the operation, for example there is no fear of causing a secondary infection, the illuminating device as a beam irradiating means, can be moved to the desired light concentration position so a to thereby directly emit the wave beam from the light device to control the light concentration position.

Figures 6, 6A:
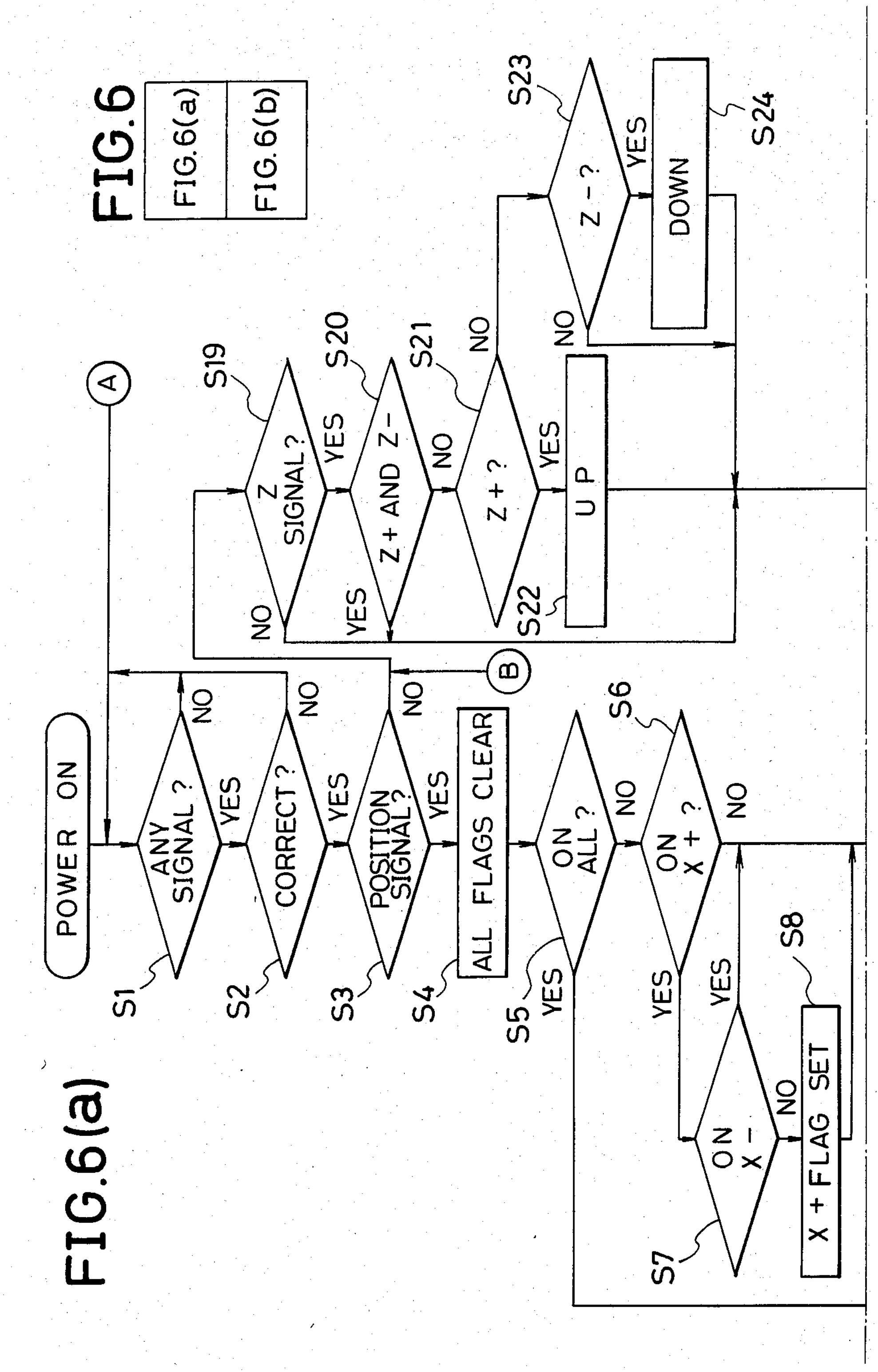
FIGS. 6, *6a* and *6b* are a flowchart describing the operation of the CPU 7 shown in FIG. 5.
Figure 6B:
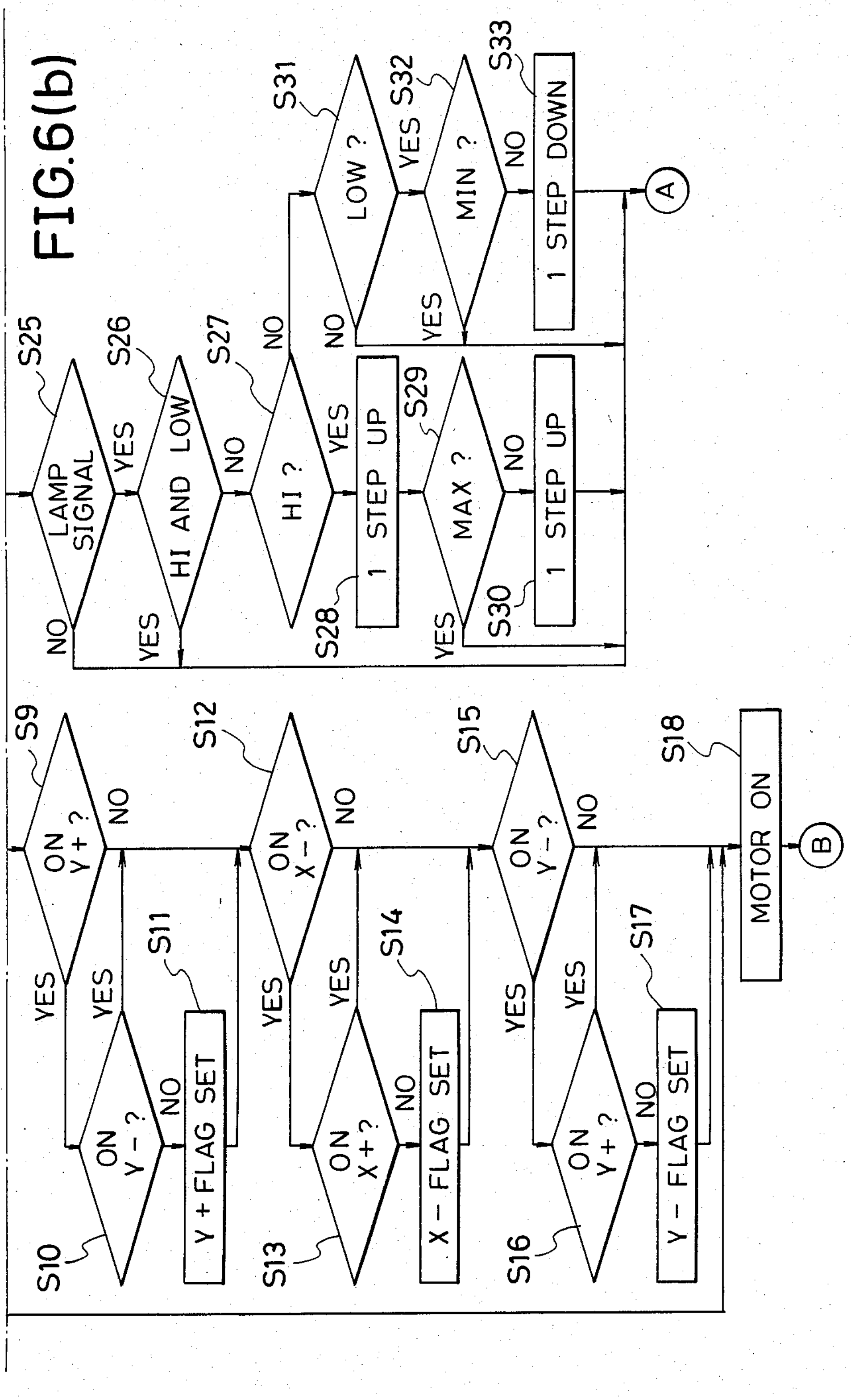

The operation of the CPU 7 will be described in detail hereafter, with reference to the flowchart shown in FIG. 6. At the first step after the system is turned on, the outputs from the detecting portions X+, X−, Y+, and Y− are checked in Step S1. When at least one of these outputs shows the detection of some signal, it is determined whether or not the signal is a correct signal from the illuminating device 3 in Step S2. If correct, the signal is decoded and checked as to whether or not the signal contains a position signal, in Step S3. When the answer in the Step 3 is positive, that is, the signal aims at changing the light concentration position, all flags X+, X−, Y+, and Y− are cleared in Step 4.

If all of the detecting portions output signals, no flag is to be set because an illuminating beam spot must be focused on the center of the receiving unit 4. In that case, the CPU 7 jumps from Step S5 to Step S18. Otherwise, the output from detecting portion X+ is checked in Step S6. When detecting portion X+ outputs a signal which is detected, or the spot covers some area on the X+ portion, the X+ flag is set as shown in Steps S6 and S8. However, if both portions X+ and X− output signals, neither the X+ flag nor the X− flag is to be set, as handled in Step S7, because the spot must be focused on the boundary between portions X+and X−. In the same way, the Y+ flag, the X− flag, and the Y− flag are set in Steps S9 through S17 if corresponding signals are obtained. Finally, in Step S18, the CPU 7 operates the motors M1 and M2 and moves the lighting device 1 so that the spot comes to the center of the receiving unit 4.

For example, when the X+ flag and the Y+ flag are set, the lighting device 1 is to be moved in the direction of X− and Y−, and so on.

In Step S19, it is determined whether or not the signal contains a Z signal, and when the answer is positive, that is, the signal aims at adjusting the focus, the following focus adjusting procedure is made. If the Z signal contains a Z+ component which indicates move-up, the lighting device 1 is moved up by the motor M3 as shown in Steps S21 and S22, and if the Z signal contains a Zcomponent which indicates move-down, the lighting device 1 is moved down by the motor M3 as shown in Steps S23 and S24. If the Z signal contains both Z+ and Z− components, the focus adjustment is not made as shown in Step S20.

In Step S25, it is determined whether or not the signal contains a lamp signal.

When the answer is positive, that is, the signal aims at adjusting the illumination power of the lighting device 1, the following illumination adjusting procedure is made. If the lamp signal contains a HI component which indicates high illumination, the illumination power is increased by 1 step as shown in Steps S27 and S28. The illumination power is further increased by 1 step unless the power has reached the maximum value as shown in Steps S29 and S30. If the lamp signal contains a LOW component which indicates low illumination, the illumination power is decreased by 1 step unless the power has reached the minimum value as shown in Steps S31 through S33.

When all the procedures described above are finished, the same procedures are repeated from Step S1.

As described hereinbefore, according to the shadowless type lighting equipment of this invention, since the light concentration of the lighting device is controlled in accordance with the reflected beam of a wave beam emitted from the desired portion of a patient on an operation table, the light can be accurately concentrated automatically on the desired portion of the patient without any fear of causing a secondary infection.

We claim:

1. A shadowless lighting equipment for medical use comprising:

- a means for lighting a patient positioned on an operating table;
- a means for emitting a wave beam on a predetermined portion of said patient so as to form an irradiation area thereon;
- a means for receiving a wave beam reflected from said predetermined portion of said patient and for forming an image of said irradiation area;
- a means for comparing received information regarding an image forming position by said image forming means with received information regarding a light concentration position of said lighting means and for generating an output containing information regarding a positional difference between said image forming position and said light concentration position when said former position is shifted from said later position; and a means for driving said lighting means in response to said output from said comparing means until said light concentration position is the same as said image forming position.

2. A lighting equipment according to claim 1, wherein said wave beam is an optical wave.

3. A lighting equipment according to claim 1, wherein said wave beam is an electromagnetic wave.

4. A lighting equipment according to claim 1, wherein said wave beam is an acoustical wave.

5. A lighting equipment according to claim 1, wherein said wave beam is an infrared ray beam.

6. A lighting equipment according to claim 1, wherein said wave beam is subjected to a predetermined frequency modulation so as to thereby contain information data.

7. A lighting equipment according to claim 1, wherein said image forming means is a lens.

8. A lighting equipment according to claim 1, wherein said image forming means is a pin hole member.

9. A lighting equipment according to claim 1, wherein said comparing means comprises a receiving sensor provided with a plurality of wave detecting portions arranged on an image forming surface.

10. A lighting equipment according to claim 1, wherein said means for driving the lighting means comprises first and second motors for respectively driving said lighting means in X axis and Y axis directions of a coordinate surface, and a third motor for driving said lighting means in a direction perpendicular to said coordinate surface, and first and second clutch means respectively operatively coupled to said first and second motors.

* * * * *